(12) United States Patent
Musha et al.

(10) Patent No.: US 6,741,888 B2
(45) Date of Patent: May 25, 2004

(54) METHOD AND APPARATUS FOR ESTIMATING DEGREE OF NEURONAL IMPAIRMENT IN BRAIN CORTEX

(75) Inventors: Toshimitsu Musha, Kawasaki (JP); Takashi Asada, Mitaka (JP)

(73) Assignee: Brain Functions Laboratory, Inc., Kawasaki (JP)

( * ) Notice: Subject to any disclaimer, the term of this patent is extended or adjusted under 35 U.S.C. 154(b) by 182 days.

(21) Appl. No.: 09/993,910

(22) Filed: Nov. 27, 2001

(65) Prior Publication Data

US 2002/0107455 A1 Aug. 8, 2002

(30) Foreign Application Priority Data

Dec. 18, 2000 (JP) .......................................... 2000-383581
Feb. 20, 2001 (JP) .......................................... 2001-043311

(51) Int. Cl.[7] ................................................ A61B 5/04
(52) U.S. Cl. ........................................................ 600/544
(58) Field of Search .................................. 690/544, 545, 690/546

(56) References Cited

U.S. PATENT DOCUMENTS 4,862,359 A * 8/1989 Trivedi et al. ............... 600/544
5,797,853 A * 8/1998 Musha et al. ............... 600/544

* cited by examiner

Primary Examiner—Max F. Hindenburg
Assistant Examiner—Brian Szmal
(74) Attorney, Agent, or Firm—Staas & Halsey LLP

(57) ABSTRACT

A proper frequency component of EEG is selected so that its scalp potential becomes smooth in a normal subject. When the brain function is impaired, non-uniformity of neuronal activity is detected in spatial as well as temporal fluctuations in the observed scalp potential of properly filtered EEG (usually the alpha component). The statistical parameters derived from dipolarity values of such a properly selected EEG component determine the state of the brain, in which whether the subject is normal or demented is judged in the early stage of dementia by comparing the obtained parameters with their threshold values. This invention presents a reliable, inexpensive, easy-to-handle and non-invasive method for sensitive screening of dementia and monitoring progress of dementia which also allows optimizing medication and treatment for dementia.

19 Claims, 11 Drawing Sheets

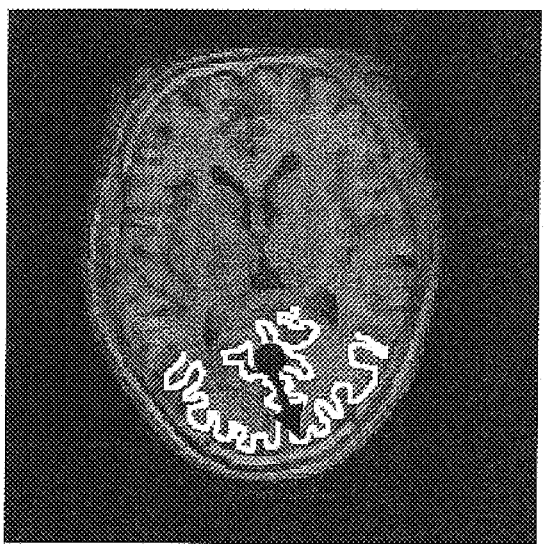
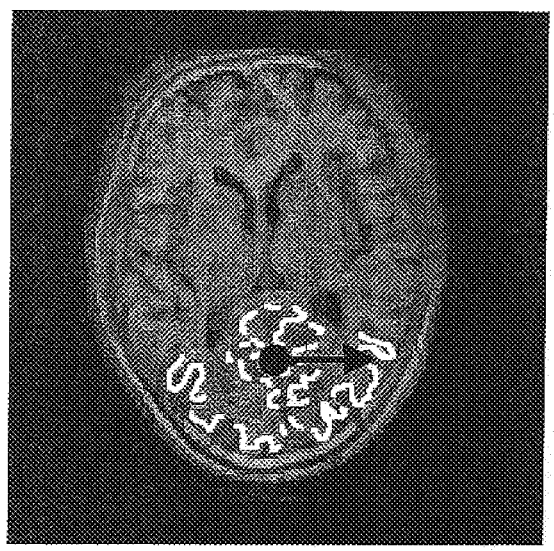
99.862 %
FIG.3A
97.057 %
FIG.3B

REALISTIC HEAD AND SINGLE EQUIVALENT DIPOLE MODEL

FIG.11

| | QUESTIONS | ANSWERS | POINTS |
|---|---|---|---|
| 1<br>(5 POINTS) | WHAT YEAR IS IT THIS YEAR?<br>WHAT SEASON IS IT NOW?<br>WHAT DAY OF THE WEEK IS IT TODAY?<br>WHAT IS THE DATE TODAY? | | |
| 2<br>(5 POINTS) | WHAT PREFECTURE IS HERE?<br>WHAT CITY IS HERE?<br>WHAT HOSPITAL IS HERE?<br>WHAT FLOOR IS HERE?<br>WHAT DISTRICT IS HERE? (e.g. KANTO DISTRICT) | PREFECTURE<br>CITY<br><br>FLOOR | |
| 3<br>(3 POINTS) | 3 NAMES OF GOODS (NO RELATION TO EACH OTHER)<br>EXAMINER CALLS A NAME OF GOODS PER SECOND, AND THEN MAKES SUBJECT REPEAT SAME.<br>GIVE 1 POINT FOR 1 CORRECT ANSWER. REPEAT UNTIL SUBJECT CALLS ALL 3 NAMES (UP TO 6 TIMES).<br>WRITE HOW MANY TIMES OF REPETITION.<br>___ TIMES | | |
| 4<br>(5 POINTS) | SEQUENTIALLY SUBTRACT 7 FROM 100 (UP TO 5 TIMES), OR MAKE SUBJECT SAY "FUJINOYAMA" REVERSELY. | | |
| 5<br>(3 POINTS) | MAKE SUBJECT REPEAT AGAIN NAMES OF GOODS PRESENTED IN ABOVE 3 | | |
| 6<br>(2 POINTS) | WHAT IS THIS? (SHOWING WATCH)<br>WHAT IS THIS? (SHOWING PENCIL) | | |
| 7<br>(1 POINT) | REPEAT THE FOLLOWING SENTENCE<br>"WE ALL PULL THE ROPE TOGETHER " | | |
| 8<br>(3 POINTS) | (ORDER OF 3 STEPS)<br>"HOLD THIS PAPER WITH YOUR RIGHT HAND"<br>"FOLD IT HALF"<br>"PUT IT ON THE DESK" | | |
| 9<br>(1 POINT) | (READ THE FOLLOWING SENTENCE, AND OBEY THE INSTRUCTIONS)<br>"CLOSE YOUR EYES" | | |
| 10<br>(1 POINT) | (WRITE ANY SENTENCE) | | |
| 11<br>(1 POINT) | (DRAW THE FOLLOWING DIAGRAM) | | |
| | | TOTAL POINTS | |

METHOD AND APPARATUS FOR ESTIMATING DEGREE OF NEURONAL IMPAIRMENT IN BRAIN CORTEX

BACKGROUND OF THE INVENTION

1. Field of the Invention

The present invention relates to a method and apparatus for estimating the degree of neuronal impairment in the brain cortex, which can be used for early estimation of a senile dementia disorder.

2. Description of the Related Art

With respect to senile dementia, it is statistically said that about 30% of nonagenarians are in dementia. This senile dementia is becoming a serious problem for the coming aging society.

Accordingly, such a dementia disorder should be preferably found as early as possible and treated before it results in a serious state. The judgment of the dementia disorder has been conventionally performed by various manual methods as follows:

(1) Hasegawa's Dementia Rating Scale (HDS)

The HDS method is devised for screening demented old people from normal aged ones. The HDS is composed of questions which the normal old or aged people without an intellectual disorder can relatively easily answer. This method can be normally performed in 5–10 minutes.

The questions include 11 items such as "memory and registration", which are main items, "orientation", "calculation", and "general common sense". Predetermined weighting are performed to the points, based on the rate of passing the question items, according to the difficulty.

Also, with revised evaluation items, the HDS is replaced with the Hasegawa's Dementia rating Scale Revised (HDS-R) in which the examination can be performed if the birthday of the person himself/herself is solely confirmed.

(2) National Mental Research Dementia Screening Test

This national mental research dementia screening test is a standardized simplified test for accurately screening old people suspected of being dementia from healthy old people.

Namely, it is a screening test which easily enables co-medical staffs led by health nurses to use, give marks, and screen the persons for the purpose of performing health activities in respective districts finding out persons suspected of being dementia at an early stage, and adequately advising and guiding them. Also, this screening test can be used for the screening at the time of epidemiology investigation.

(3) N Type Mental Function Examination

The N type mental function examination is an old people's mental function examination which aims to measure an intellectual function in wider range, by adding questions on concept formation, diagram duplication, space recognition, movement formation function, and the like to questions on memory, orientation, and calculation.

This test can be used for distinguishing whether aged change of the mental function is caused by normal aging or disordered dementia. However, this test mainly aims to be performed to the old people suspected of being demented. For this reason, the test is prepared so as to evaluate a dementia degree (level) at a wide range of 5 stages, that is, normal, boundary, slight dementia, moderate dementia, and severe dementia.

(4) Mental Status Questionnaire (MSQ)

This MSQ (Mental Status Questionnaire) has been developed for a large scale investigation of old people at homes in New York City in 1958. Since the investigation is for many people socially, physically, and mentally quite different from each other, the aim of the investigation is to be performed simply, objectively, and easily, and to provide a reliable index for a mental function disorder.

As for question items of the MSQ, most distinguishable ones have been selected from among the question items including an orientation, a memory, a calculation, general and personal information by a preparatory test for hundreds of people. One half of the question items are composed of those for testing the orientation, while the other half question items are composed of those for testing a general memory, so that the emphasis is laid on the orientation test.

(5) Mini-Mental State Examination (MMSE)

This MMSE has been developed in a short and standardized scale for a neurophysiological examination of inpatients as shown in FIG. 11.

Other various action observation scales (observation method) have been proposed as follows:

(6) Ezawa's "Clinical Judgment Criteria of Senile Intelligence";

(7) Functional Assessment Staging Test (FAST);

(8) Clinical Dementia Rating (CDR);

(9) GBS Scale;

(10) N Mental State Scale For Old People (NM Scale).

Among above-mentioned prior art dementia judgment methods, it is found that the MMSE is a method securing a fixed reliability since the smaller the MMSE score on the abscissa in FIG. 1 becomes, the neuronal loss ratio N obtained from autopsy becomes larger, so that the mutual relationship is assured. However, since this method adopts a test form in which doctors always examine subjects (patients) in interviews, there have been problems as follows:

① Since a questioner exists, the answer greatly depends on the special human relationship between the questioner and the subject, and is not always objectively and accurately obtained, resulting in variation of the judgment result.

② While the subject is repeating the test, he or she may learn the examination contents, so that the objective judgment result can not be obtained.

③ The subject occasionally refuses to answer.

Thus, in the prior art diagnosis methods, an objective method for distinguishing an early-stage demented patient from a normal person has not been proposed. Furthermore, in order to use it for dementia screening, the diagnosis method must be performed in a short time, at a low cost, and treated easily. However, a practicable method which enables the diagnosis of the demented patient at an early stage has not yet been proposed by the prior art methods including the above-mentioned methods.

Also, the methods utilizing the above-mentioned SPECT, PET, and the like need extremely short-life radioisotope materials, a cyclotron is required as a part of this system, which results in a greatly high cost.

SUMMARY OF THE INVENTION

It is accordingly an object of the present invention to provide inexpensive method and apparatus for estimating the degree of neuronal impairment in the brain cortex, which enable an objective judgment of an early dementia disorder without men's intervention for the judgment.

It has been widely known that human thinking, recognition, recall of memory, pleasantness/unpleasantness, mental fatigue, stress, and the like depend on an electrical action of a number of neurons in the brain.

Namely, it has been thought that signal transmission in a brain is performed by transmission of active potential impulses on nerve axons, and that the contents of the signal are encoded to a frequency of the impulses. When the action potential impulse reaches an excitatory synapse, electric current flows out of the connected neuron, through tissues outside the neurons, and returns to the original cell body. Since the current flow closely resembles that of a single current dipole, the electrical action of an individual neuron can be replaced with a single equivalent current dipole.

If activated neurons concentrate on a relatively limited place, their electric activity can be approximated by one or more such equivalent current dipoles.

In order to find out such current dipoles, the potentials (or magnetic field strengths) which appear at the positions of EEG (MEG) sensors on a scalp at the time when one or more current dipoles having an arbitrary moment are arbitrarily placed in the head are calculated, and the mean squared value of the errors between the calculated potentials and the potentials (or magnetic fields) measured by the sensors is calculated.

The current dipoles are moved until the position, the direction, and the value where the mean value of the squared errors becomes least are obtained, which is made an equivalent dipole.

If non-uniformity occurs in the neuronal activity in the cortex as a result of Alzheimer's disease, this non-uniformity appears in the scalp potential. Since the scalp potential distribution is smooth, deviations from this smooth potential given as is mean square value reflect non-uniform neuronal activity in the cortex. This smoothness is numerically given by the mean dipolarity (approximate degree of equivalent dipole for measured potential) over a given period of time.

The present invention is based on well-known technologies indicated in the Japanese Patent Publication No.3-42897, the Japanese Patent Application Laid-open No.3-99630, the Japanese Patent No.2540728, and the like.

In the present invention developed from those basic technologies, it has become clear that a moment of a stochastic process, which is a statistic on time variation of the dipolarity, or the mean dipolarity on an alpha wave has a threshold value by which normal can be distinguished from dementia. Accordingly, it becomes possible to quantify dementia, in particular, Alzheimer's disease, and to distinguish normal from dementia at a certain sensitivity and specificity.

Furthermore, the mean dipolarity fluctuates in time. This reflects the instability (standard deviation) of the neuronal activity. The instability generally increases along with the progress of dementia. The standard deviation indicating the fluctuation of such a mean dipolarity also has a threshold value, in which if the standard deviation becomes larger than the threshold value, the subject can be estimated as Alzheimer's disease.

The relationship between such a mean dipolarity "d" and a standard deviation SD is shown in a brain impairment diagram of FIG. 2. Threshold values of the mean dipolarity and standard deviation divide the diagram in four domains ①–④. The second and fourth quadrants ②, ④ indicate Alzheimer's disease and normal, respectively.

FIGS. 3A and 3B show MRI cross-sections of the head, and show the dipolarity values obtained by a computer simulation, where neurons in white zones are activated. FIG. 3A shows a normal example, in which neuronal activity is uniform over the white zone and the mean dipolarity indicates a large value "99.862" although the activated neurons spread over such a large part. Also, FIG. 3B simulates Alzheimer's brain where white zones are separated by inactive neurons, in which the mean dipolarity is as low as "97.057".

Accordingly, by obtaining the above-mentioned mean dipolarity "d" for each equivalent dipole, the mean dipolarity "d" and the neuron loss rate N can be graphed as shown by the characteristic curves in FIG. 1. The curve N is estimated from autopsy results of Alzheimer's patients and their clinical data before autopsy.

Also, it has been clarified by the above-mentioned SPECT that the mean dipolarity of the alpha component is highly correlated to cerebral blood flow rate in specified regions of the cortex as the temporal and the temporal-parietal lobes, which is specific to the early Alzheimer's disease.

On the other hand, in case a brain wave such as an alpha wave is measured by using the brain sensor or the brain magnetic sensor, two equivalent dipoles can be adopted since it is thought that the source of the wave is distributed over both hemispheres of the brain. However, even though two equivalent dipoles are required in order to specify the position of the active neuron, a single equivalent dipole is enough to judge the dipolarity.

Therefore, the inventor of the present invention separately has analyzed, as shown in FIGS. 4–7 for example, the case where the head is supposed to be a spherical shape (see FIGS. 4 and 6) and the case where the head is made a real shape (see FIGS. 5 and 7), in two models of the case where a single equivalent dipole is supposed (see FIGS. 4 and 5) and the case where two equivalent dipoles are supposed (see FIGS. 6 and 7), whereby it has been found that the envelopes connecting the peak values of the dipolarity values of the alpha component in the respective cases are consistent with each other.

Namely, in case of a single equivalent dipole, the location of the equivalent dipole vector is near a midline of the head which is different from the case of two equivalent dipoles. However, it has been found that the peak values of the mean dipolarities "d" do not have mutually much difference, and that whether the peak values are obtained for the real shape or the spherical shape does not make much difference.

A method for estimating degree of neuronal impairment in brain cortex is characterized in that a scalp potential of a subject is detected by mounting a plurality of EEG sensors on the scalp of a subject, the scalp potential is converted into numerical data to obtain a dipolarity, a statistic on a time variation of the dipolarity is obtained as dementia degree parameters of the subject, and the parameters are outputted.

Furthermore, in the method for estimating degree of neuronal impairment in brain cortex according to the present invention, the scalp potential may be detected by a terminal equipment, the data of the scalp potential may be sent to an operation center through a communication line, and the parameters required for a dementia estimation may be determined at the operation center to be sent back through the communication line to the terminal equipment for outputting.

An apparatus for preparing the neuronal impairment diagram according to the present invention may comprise a plurality of EEG sensors mounted on a scalp of a subject, a computing unit for converting an output signal of the EEG sensors into numerical data to obtain a dipolarity and for obtaining statistic on a time variation of the dipolarity as dementia degree parameters of the subject, and an output unit for outputting the parameters.

Furthermore, in the apparatus for estimating degree of neuronal impairment in brain cortex according to the present invention, the EEG sensor and the output unit may be provided in a terminal equipment, the computing unit may be provided in an operation center, and the terminal equipment and the operation center may be connected through a communication line.

The present invention may provide a program to be executed by a computer. For automatically judging a brain action, the program is provided with the steps of determining a dipolarity based on numerical data of a scalp potential of a subject detected by mounting a plurality of EEG sensors or MEG sensors on a scalp of the subject, judging a statistic on a time variation of the dipolarity as dementia degree parameters of the subject, and outputting the parameters.

Also, the present invention may provide a computer readable recording medium characterized in that the above-mentioned program is recorded.

Various modes may be applied to the above-mentioned method, apparatus therefor, program therefor, and recording medium therefor, as follows:

The above-mentioned dipolarity may comprise a value indicating an approximate degree, after a predetermined frequency component within the data is extracted, and based on the predetermined frequency component, at a time when one or more equivalent dipoles are determined in which a mean value of a squared error between a potential distribution which one or more current dipoles, supposed in the head, form at positions of the sensors and a measured potential of the sensors indicated by the data becomes minimized.

A spherical head model may be applied to the head in this case.

As the statistic, a moment of a stochastic process or a mean dipolarity indicating a mean value of a fixed number of peak values at a time when a plurality of dipolarities are obtained by sampling may be used. Alternatively, since a standard deviation increases as the mean dipolarity decreases with a high degree of correlation, the standard deviation indicating the fluctuation can be used instead of the mean dipolarity to obtain the same result.

The mean dipolarity or the standard deviation may be obtained by using a signal within a predetermined frequency component, not only the alpha component.

The data may be obtained by using an MEG sensor instead of the EEG sensor, and a magnetic field instead of the potential.

Also, whether the subject is normal or demented may be judged by comparing the mean dipolarity value with a predetermined threshold value, by comparing the standard deviation with a predetermined threshold value, or by a mutual relationship between the mean dipolarity and the standard deviation.

In addition, a kind and a degree of dementia may be judged by a relationship between the mean dipolarity and the standard deviation.

The dipolarity values can be derived based on a plural number of equivalent dipoles with a more complex head model although calculation becomes more complex.

The present invention is superior to other existing diagnosis tools as MMSE, SPECT, etc. in high reliability, high sensitivity, easy operation, non-invasiveness, short required time, and low cost.

BRIEF DESCRIPTION OF THE DRAWINGS

FIGS. 3A and 3B are diagrams showing a single equivalent dipole obtained at a head section of a normal person and a demented person;

FIG. 11 is a chart showing a prior art mini-mental state examination (MMSE).

Throughout the figures, like reference numerals indicate like or corresponding components.

DESCRIPTION OF THE EMBODIMENTS

Figure 8:
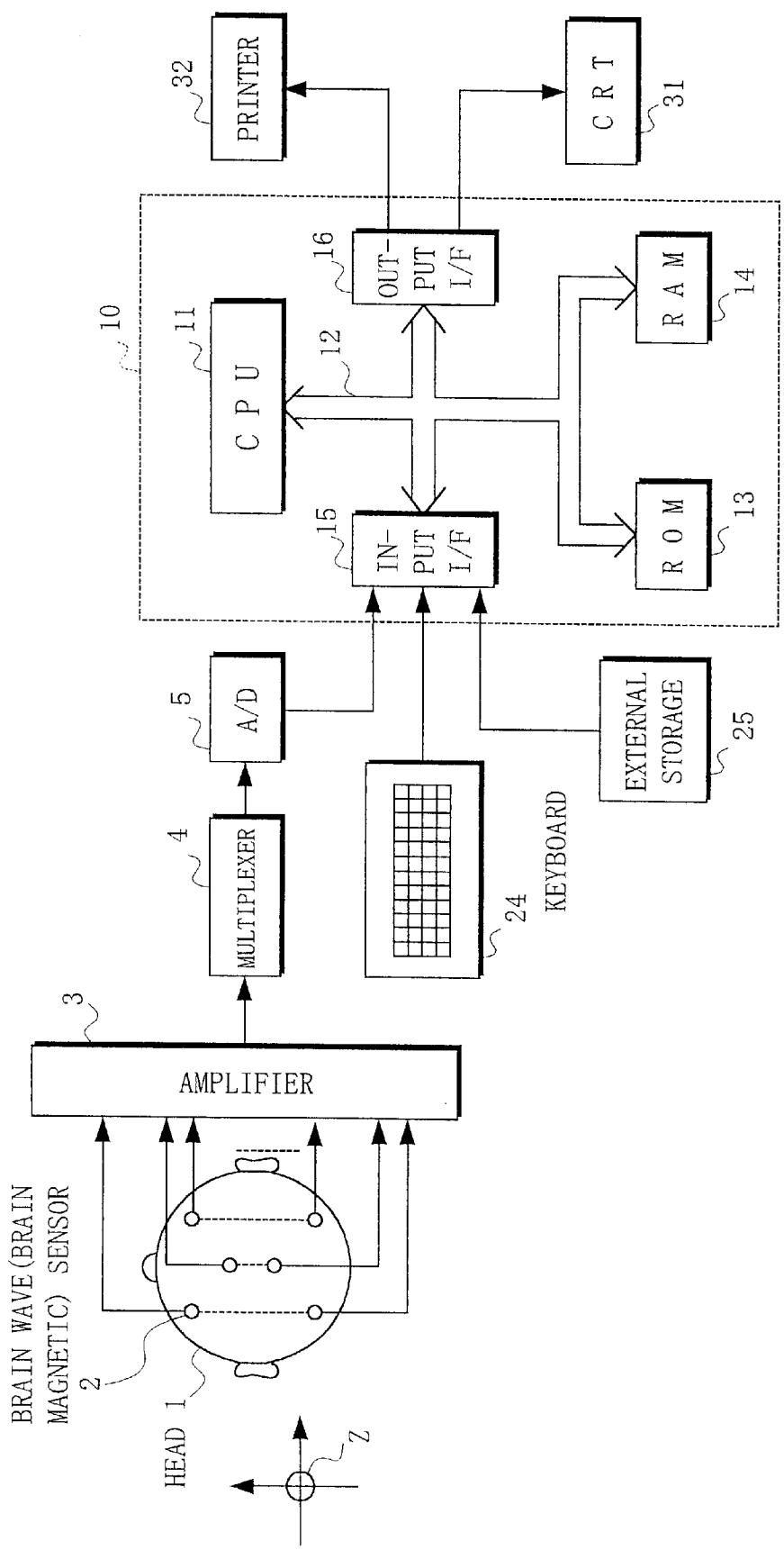
FIG. 8 is a block diagram showing an embodiment of the present invention.

FIG. 8 shows one embodiment for automatically estimating degree of neuronal impairment in brain cortex and an apparatus therefor according to the present invention.

In this embodiment, a group of EEG sensors or MEG sensors 2 comprising e.g. 21 sensors is firstly mounted on a head 1 to measure scalp potentials, or a subject puts on a cap where the sensors are properly arranged. It is to be noted that the sensors in this case may be arranged according to the international 10–20 standard even if the head is supposed to be a spherical shape.

The measured potential from the sensor 2 is supplied to an analog/digital (A/D) converter 5 through an amplifier 3 and a multiplexer 4, so that the digitized measured potential (EEG) data are supplied to a computer 10 through an input interface (I/F) 15. It is to be noted that the input interface 15 performs the Fourier transform to the data to execute a predetermined filtering process, thereby taking out only the alpha component and enabling the following processes. It should be noted that the present invention is not limited to the alpha component.

In the computer 10, a CPU 11 is connected to an ROM 13, an RAM 14, an input interface 15, and an output interface 16 through a bus 12.

The above-mentioned ROM 13 is a medium storing the above-mentioned program and the like for determining the equivalent dipole, and the RAM 14 is a memory for storing EEG data from a digitizer 23, a keyboard 24, and the A/D converter 5.

Figure 9:
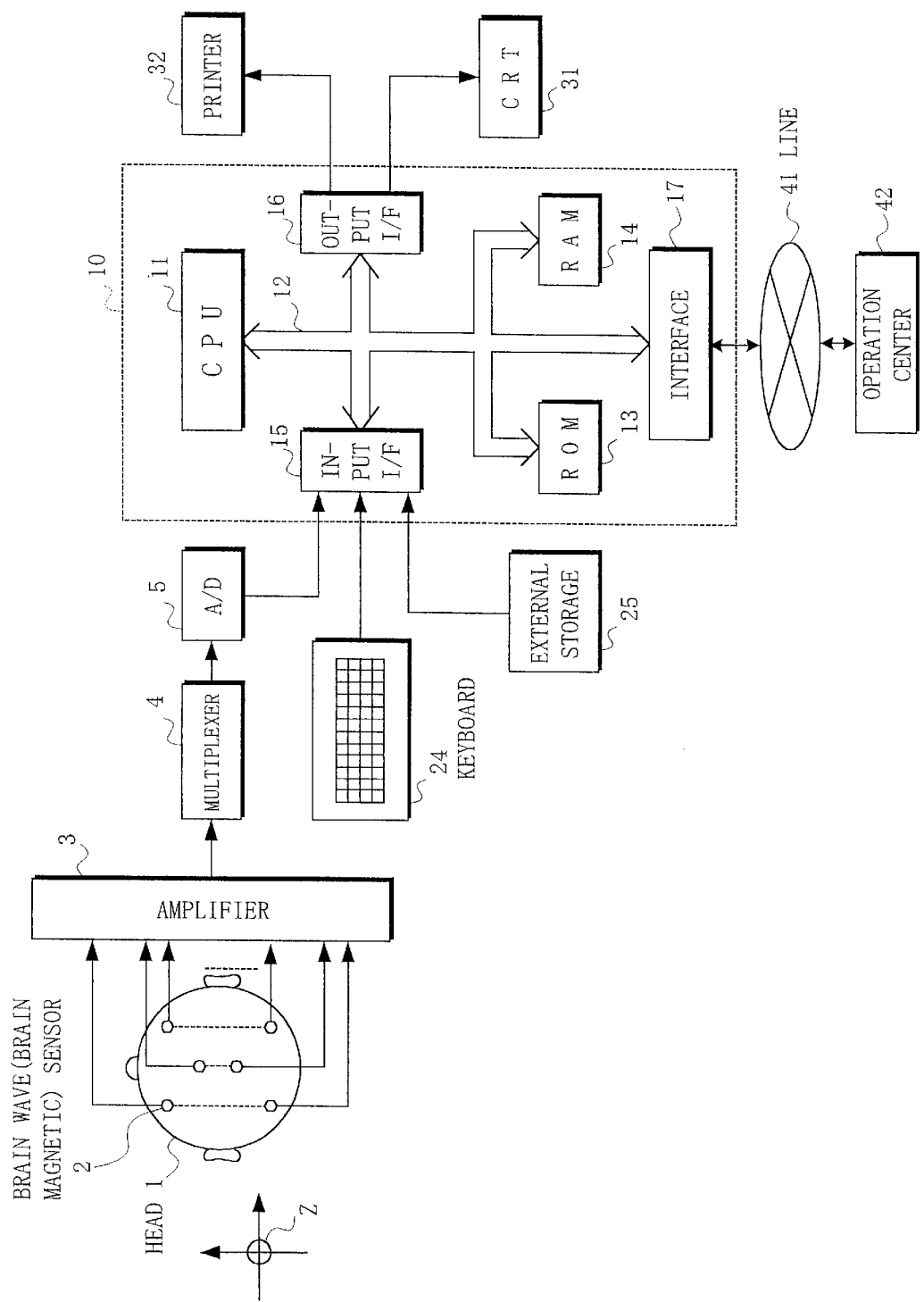
FIG. 9 is a block diagram showing a modification of the present invention.

It is to be noted that such an arrangement as in the following may be employed: The brain wave data, as shown in FIG. 9, are sent from an interface 17 of the computer 10 serving as a data transfer terminal equipment only in this case to an operation center 42, as a computing (arithmetic) unit through a communication line 41 of the Internet or the like, where the result analyzed at the operation center 42 is again sent back to the computer 10 in the clinical spot through the communication line 14, and the result is outputted from an output unit such as a CRT 31 and a printer 32, so that a doctor utilizes the result as the materials for a diagnosis. In this case, the program and the recording medium are provided in the operation center.

Figure 1:
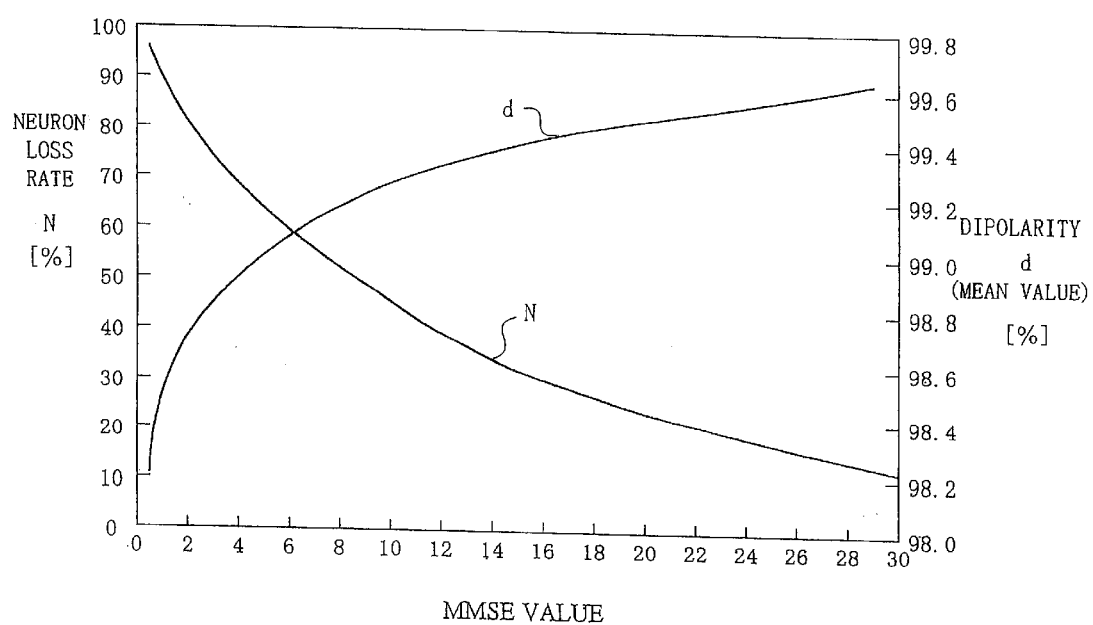
FIG. 1 is a graph, obtained by the inventor of the present invention, showing a dipolarity (mean value) "d" and a neuron loss rate N for an MMSE value.
Figure 2:
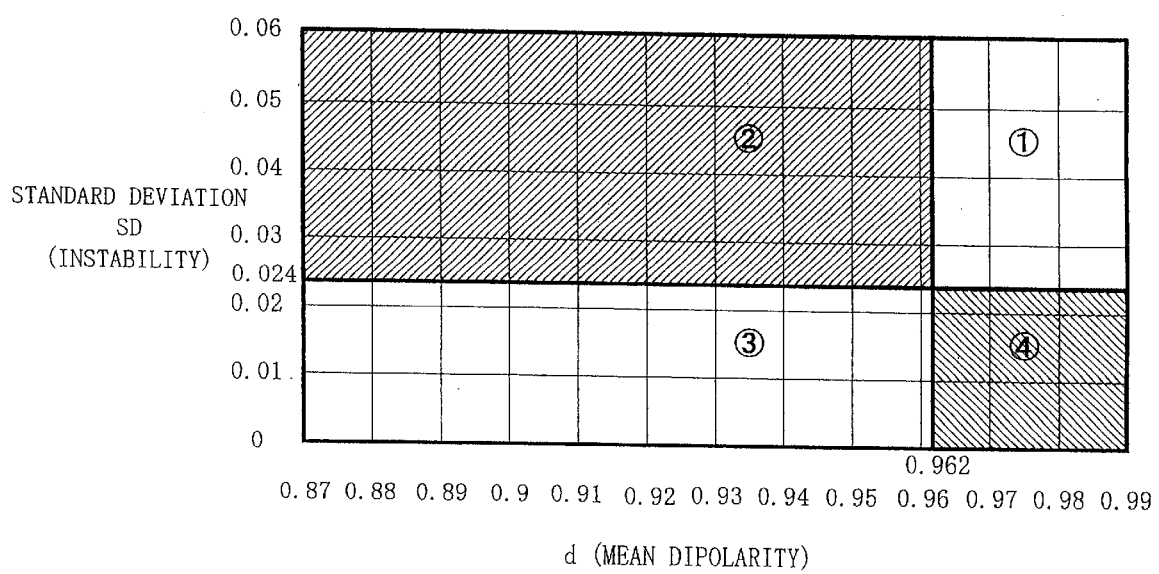
FIG. 2 is a neuronal impairment diagram, obtained by the inventor of the present invention, showing a relationship between a mean dipolarity and its standard deviation for judging normal/dementia.
Figure 4:
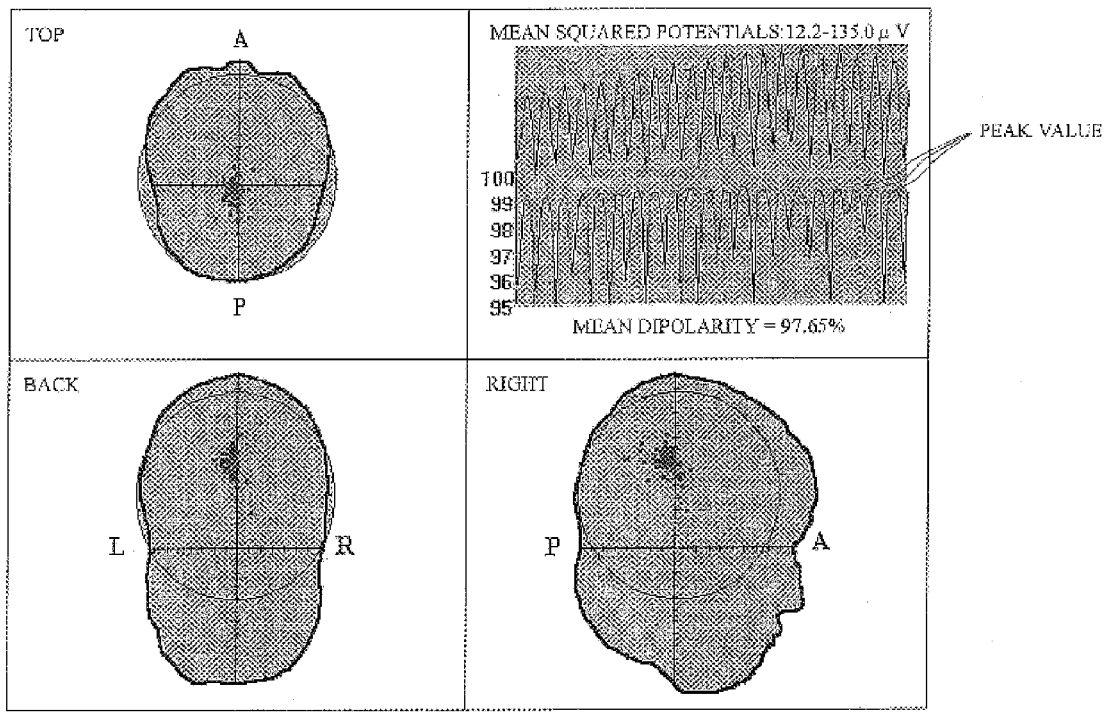
FIG. 4 is a graph showing a dipolarity of a single equivalent dipole calculated on a spherical head model of a uniform conductor in order to generate the neuronal impairment diagram, an apparatus therefor, a program therefor, and a recording medium therefor according to the present invention.
Figure 5:
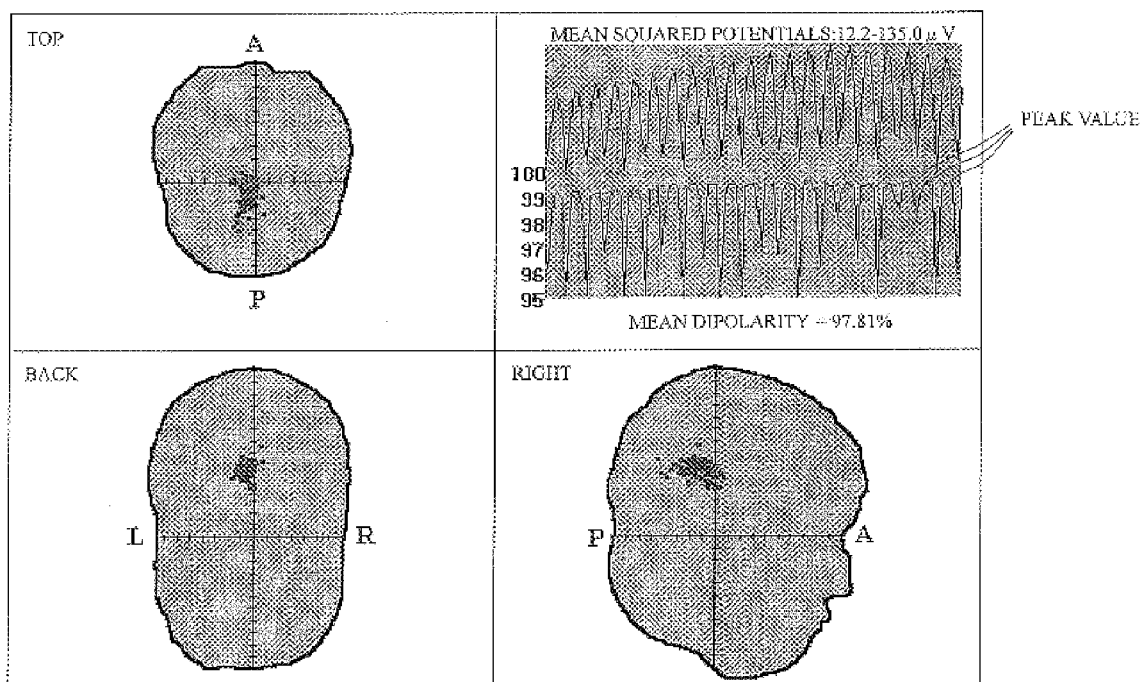
FIG. 5 is a graph showing a dipolarity in case a head is supposed to be a real shape and a single equivalent dipole is used in order to realize the present invention.
Figure 6:
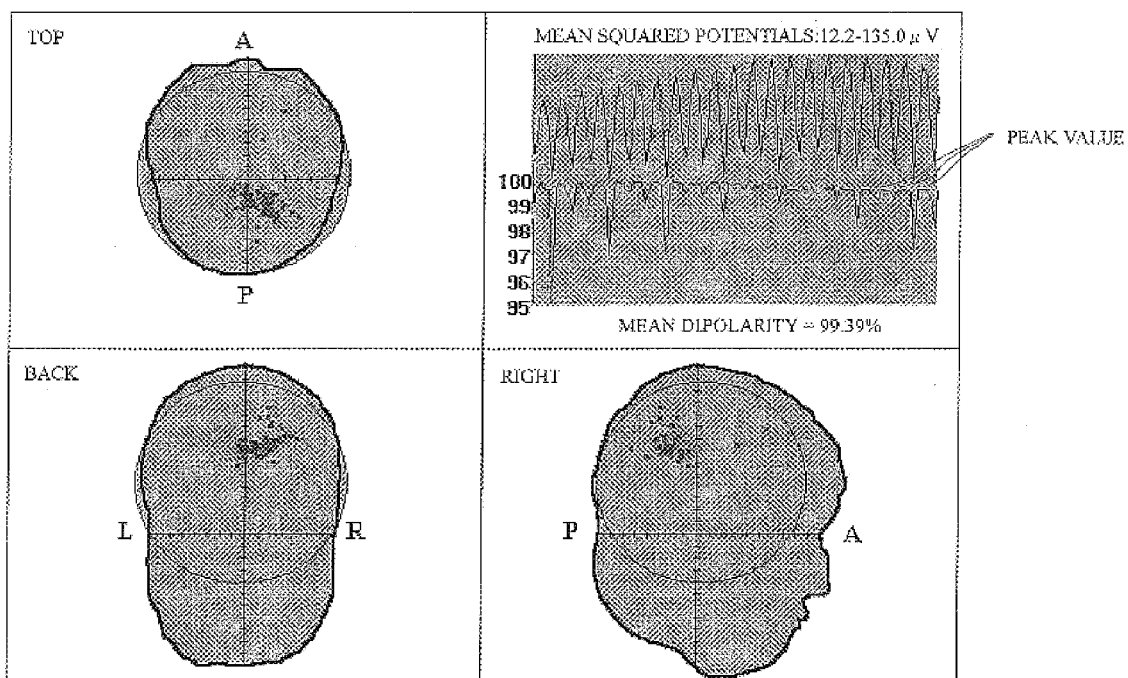
FIG. 6 is a graph showing a dipolarity in case a head is supposed to be a spherical shape and two equivalent dipoles are used in order to realize the present invention.
Figure 7:
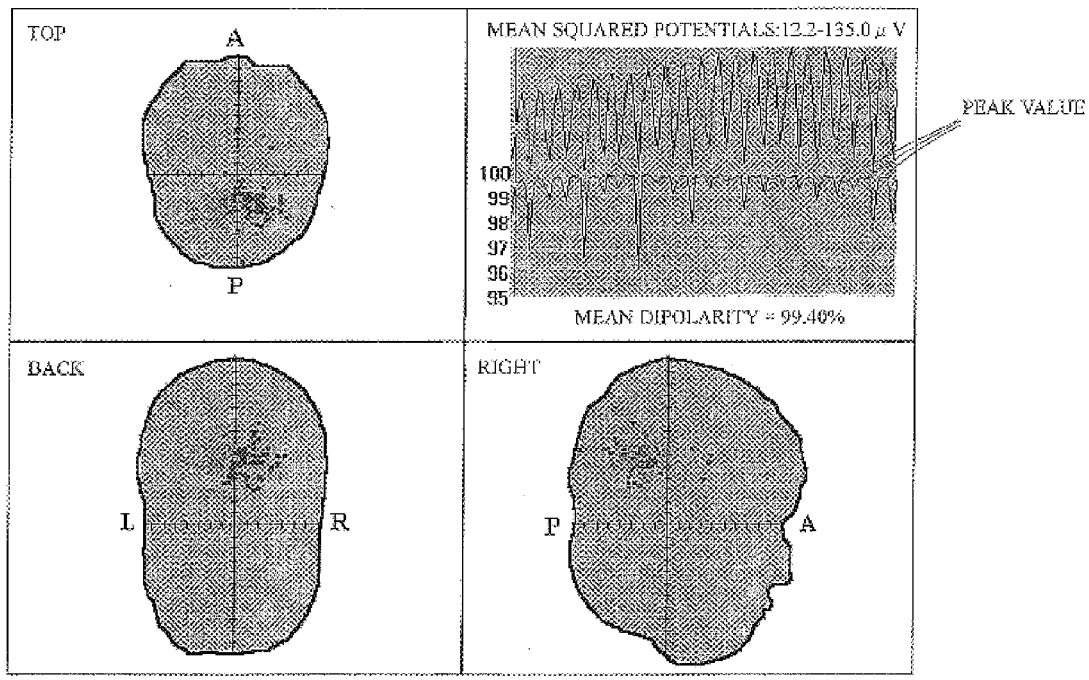
FIG. 7 is a graph showing a dipolarity in case a head is supposed to be a real shape and two equivalent dipoles are used in order to realize the present invention.

An external storage 25 storing characteristic data of the graphs shown in FIGS. 1 and 2 is connected to the input interface 15. The display 31 of the CRT or the like which displays the operation result (MMSE value as the dementia degree) of the computer 10 and the printer 32 printing the data and the waveform displayed at the display 31 are connected to the output interface 16 as output units. It is to be noted that the all of the programs and the like may be stored only in the ROM 13 without using the external storage 25.

Figure 10:
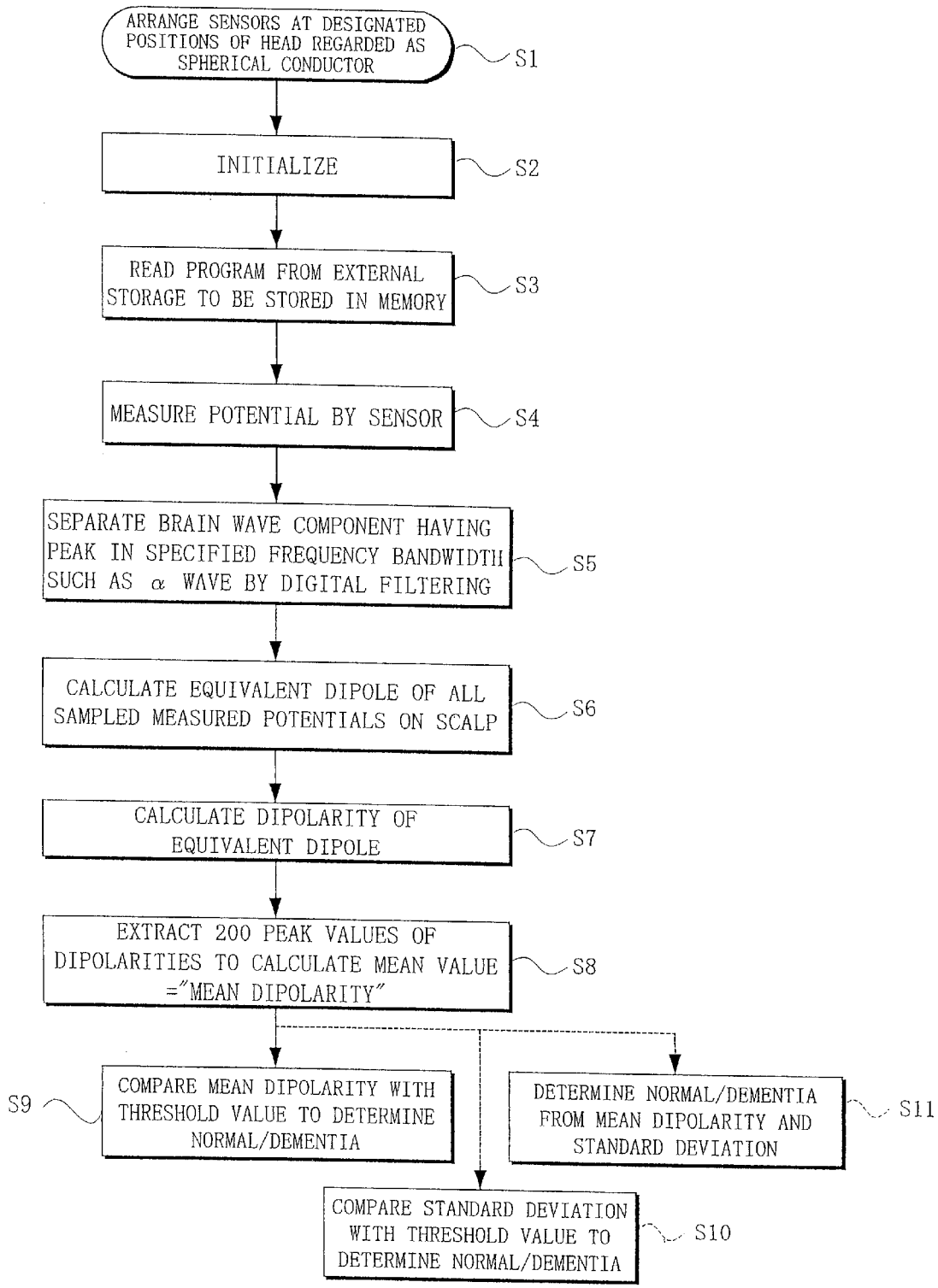
FIG. 10 is a flow chart showing a process procedure of a computing unit used in the present invention.

The operation of the embodiments in the above-mentioned arrangement will now be described referring to the flow chart shown in FIG. 10.

After the sensors 2 are firstly arranged (at step S1) on the head 1 as shown in FIGS. 8 and 9, the computer 10 is initialized with a power source (not shown) being made "on" (at step S2).

Then, the programs for various operations, those for signal processing, and the like are read out of the external storage 25 to be stored in the RAM 14 of the computer 10 (at step S3). Such programs may be preliminarily stored in the ROM 13 that is a nonvolatile memory in the computer 10.

Then, the potential measurement based on the neuronal activation in the brain is performed at a fixed sampling interval by the sensors 2 having 21 sensors mounted on the head 1 (at step S4).

Hereafter, the EEG component having the peak in the specific frequency bandwidth such as the alpha band is separated by the digital filtering process (at step S5).

The equivalent dipoles for all of the sampled measured potentials on the scalp are calculated (at step S6).

Namely, at step S6, as mentioned above, the CPU 11 of the computer 10 calculates the potential ($V_c$) at the electrode positions on the scalp generated by e.g. a single current dipole in case the current dipole is supposed to be placed at a predetermined position in the head, the mean value of the squared error with the potential ($V_m$) measured at step S4 is obtained, the position and the moment of the current dipole which make the mean value of the squared error are obtained, and such processes are repeated until the squared error converges to be equal to or less than the reference value. When the squared error converges to become equal to or less than the reference value, the current dipole at the position is made an equivalent dipole to store the position in the RAM 14.

Hereafter, the dipolarity is calculated (at step S7). Namely, a dipolarity "d" (not yet the mean value at this point) indicating to what extent the equivalent dipole approximates to the measured potential is calculated as shown in the following equations (1) and (2).

$$d = \sqrt{1 - \frac{\sum_{i=1}^{M}(V_{mi} - V_{ci})^2}{\sum_{i=1}^{M}V_{mi}^2}} \quad \text{Eq. (1)}$$

$$d = \sqrt{1 - \frac{\left\{\sum_{i=1}^{M}(V_{mi} - V_{ma})(V_{ci} - V_{ca})\right\}^2}{\sum_{i=1}^{M}(V_{mi} - V_{ma})^2 \sum_{i=1}^{M}(V_{ci} - V_{ca})^2}} \quad \text{Eq. (2)}$$

It is to be noted that in the above-mentioned equations (1) and (2), M indicates the number of the sensor 2, and $V_{ma}$ and $V_{ca}$ respectively indicate the mean values of the measured values and calculated values.

Thus, a fixed number of peak values (see FIGS. 3–6), e.g. 200 peak values, of the dipolarity values "d" obtained for each of the measured potentials on the scalp sampled e.g. per 10 ms are extracted to obtain the mean value="mean dipolarity or mean alpha dipolarity" (at step S8).

The mean alpha dipolarity is compared with a predetermined threshold value. When the mean alpha dipolarity is more than the threshold value, the subject is judged to be normal. On the other hand, when it is less than the threshold value, the subject is judged to be a dementia state (at step S9). Alternatively, the standard deviation is compared with the threshold value, so that whether it is normal or demented is judged (at step S10). Or zones of which boundaries depend on the reliability percentage of the judgment, where the relation between the threshold values and the reliability percentage is determined from the sensitivity-specificity curves, replace threshold values.

Alternatively, in the brain deterioration graph of FIG. 2 showing the relationship between the mean dipolarity "d" and the standard deviation SD, the subject is judged to be Alzheimer's disease in the 2nd quadrant ②, and the subject is judged to be normal in the 4th quadrant ④ (at step S11). These judgment results are outputted to the CRT 31 or the printer 32 as an output unit. According to the clinical data so far, the sensitivity and specificity by this method is about 70%.

As described above, the method for estimating degree of neuronal impairment in brain cortex, an apparatus therefor, a program therefor, and a recording medium therefor according to the present invention are arranged so that whether a subject is normal or demented is immediately and objectively determined by statistical properties of dipolarity peak values. In these processes one or more equivalent dipoles are determined in which a mean value of squared errors between a potential distribution which one or more current dipoles, supposed in the head, form at positions of the EEG sensors and a measured potential assumes least; e.g. at least one of a mean value (mean dipolarity) of a fixed number of peak values at a time when a plurality of dipolarity peak values are obtained by sampling, and a standard deviation indicating a fluctuation of the peak values.

Also, when the subject is judged to be demented, the degree of dementia can be evaluated. In addition, since the effect of the dosage for dementia and a cognitive rehabilitation can be numerically evaluated, the optimum medication for each patient can be selected, the dosage in terms of quantity and frequency can be determined in a short time, and the optimum method of various cognitive rehabilitation can be applied.

The change of the mean value of the dipolarity values before and after the therapy by the medication, the cognitive rehabilitation, and the like enables the respective efficiency thereof to be measured.

Also, it is possible to predict the future progress of dementia degree by the analysis of time variation of the dipolarity for the alpha wave.

Different from the judgment result of the prior art examination method, it becomes possible to objectively, accurately, and promptly judge the dementia degree of the subject with a low-cost apparatus, so that the specific effects can be obtained as follows:

(1) By the EEG measurement in about three minutes, the progress state of Alzheimer's disease can be monitored.

(2) Screening of demented patients in the early stage can be simply performed to all of the senile. Since the therapy at an early stage is effective for delaying the onset of dementia, it contributes to the control of the senile dementia population. This greatly contributes to the economic effect and the load reduction of the family who nurses the patient.

(3) Since the effect of a medicine presumed to be useful to the progress control or therapy of Alzheimer's disease is immediately measured, it can be utilized for a development of a new medicine relating to Alzheimer's disease.

(4) The effects of various therapies such as art therapy, music therapy, and gardening therapy can be objectively measured.

(5) The degree of dementia can be objectively recognized.

(6) Application to the screening of dementia can be easily made non-invasively.

What we claim is:

1. A method for estimating a degree of neuronal impairment in a brain cortex, comprising:
   detecting scalp potentials of a subject by mounting a plurality of EEG sensors or MEG sensors on a head of the subject,
   converting scalp potentials or magnetic fields into data to obtain a dipolarity,
   obtaining a statistic on a time variation of the dipolarity as a dementia degree of the subject, and
   outputting the parameters,
   wherein the statistic comprises a mean dipolarity indicating a mean value of a fixed number of peak values at a time when a plurality of dipolarities are obtained by sampling and a standard deviation indicating a fluctuation of the peak values, and whether the subject is normal or demented is estimated by a mutual relationship between the mean dipolarity and the standard deviation.

2. The method for estimating a degree of neuronal impairment in a brain cortex as claimed in claim 1, wherein the dipolarity comprises a value indicating an approximate degree, after a predetermined frequency component within the data is extracted, and based on the predetermined frequency component, at a time when one or more equivalent dipoles are determined in which a mean value of a squared error between a potential distribution which one or more current dipoles, supposed in the head, form at positions of the sensors and a measured potential of the sensors indicated by the data becomes a minimum.

3. The method for estimating a degree of neuronal impairment in a brain cortex as claimed in claim 2, wherein the head comprises a spherical model.

4. The method for estimating a degree of neuronal impairment in a brain cortex as claimed in claim 1, wherein the mean dipolarity and the standard deviation are obtained by using a signal within an alpha frequency bandwidth as the predetermined frequency component.

5. The method for estimating a degree of neuronal impairment in a brain cortex as claimed in claim 4, wherein a kind and a degree of dementia are judged by a relationship between the mean dipolarity and the standard deviation.

6. The method for estimating a degree of neuronal impairment in a brain cortex as claimed in any one of claims 1, 2, 3, and 4, wherein scalp potentials are detected by a terminal equipment, the data are sent to an operation center through a communication line, and the necessary parameter values are sent back through the communication line to the terminal equipment for estimation of dementia.

7. An apparatus for estimating a degree of neuronal impairment a in brain cortex comprising:
   a plurality of EEG sensors or MEG sensors mounted on a head of a subject to detect scalp potentials of the subject,
   a computing unit to convert output signals of the EEG sensors into data to obtain a statistical on a time variation of dipolarity as dementia degree parameters of the subject, and
   an output unit to output the parameters,
   wherein the statistic comprises a mean dipolarity indicating a mean value of a fixed number of peak values at a time when a plurality of dipolarities are obtained by sampling and a standard deviation indicating a fluctuation of the peak values, and whether the subject is normal or demented is estimated by a mutual relationship between the mean dipolarity and the standard deviation.

8. The apparatus for estimating a degree of neuronal impairment in a brain cortex as claimed in claim 7, wherein the computing unit extracts a predetermined frequency component within the data, and, based on the predetermined frequency component, uses a value indicating an approximate degree, as the dipolarity, at a time when one or more equivalent dipoles are determined in which a mean value of a squared error between a potential distribution which one or more current dipoles, supposed in the head, form at positions of the sensors and a measured potential of the sensors indicated by the data becomes a minimum.

9. The apparatus for estimating a degree of neuronal impairment in a brain cortex as claimed in claim 8, wherein the head comprises a spherical model.

10. The apparatus for estimating a degree of neuronal impairment in a brain cortex as claimed in claim 7, wherein the computing unit obtains the mean dipolarity value and the standard deviation of dipolarity values around the mean within the alpha frequency bandwidth as the predetermined frequency component.

11. The apparatus for estimating a degree of neuronal impairment in a brain cortex as claimed in claim 10, wherein the computing unit judges a kind and a degree of dementia by a relationship between the mean dipolarity and the standard deviation.

12. The apparatus for estimating a degree of neuronal impairment in brain cortex as claimed in any one of claims 7, 8, 9, and 10, wherein the sensor and the output unit are provided in a terminal equipment, the computing unit is provided in an operation center, and the terminal equipment and the operation center are connected to each other through a communication line.

13. A computer program for estimating degree of neuronal impairment in a brain cortex, and making a computer execute:
   determining a dipolarity based on data of scalp potentials of a subject detected by mounting a plurality of EEG or MEG sensors on a head of the subject,
   determining a statistic on a time variation of the dipolarity as dementia degree parameters of the subject, and
   outputting the parameters, wherein the statistic comprises a mean dipolarity indicating a mean value of a fixed number of peak values at a time when a plurality of dipolarities are obtained by sampling and a standard deviation indicating a fluctuation of the peak values, and whether the subject is normal or demented is estimated by a mutual relationship between the mean dipolarity and the standard deviation.

14. The computer program as claimed in claim 13, wherein the dipolarity indicates an approximate degree, after a predetermined frequency component within the data is extracted, and based on the predetermined frequency component, at a time when one or more equivalent dipoles are determined in which a mean value of a squared error between a potential distribution which one or more current dipoles, supposed in the head, form at positions of the sensors and a measured potential of the sensors indicated by the data becomes a minimum.

15. The computer program as claimed in claim 14, wherein the head comprises a spherical model.

16. The computer program as claimed in claim 1, wherein the mean dipolarity or the standard deviation is obtained by using a signal within the predetermined alpha frequency band.

17. The computer program as claimed in claim 16, wherein a kind and a degree of dementia are judged by a relationship between the mean dipolarity and the standard deviation.

18. A computer readable recording medium for recording the program as claimed in any one of claims 13, 14, 15, and 16.

19. A method for estimating a degree of neuronal impairment in a brain cortex, comprising:

detecting scalp potentials on a head of a subject and obtaining a dipolarity based on the detected scalp potentials; and obtaining a statistic on a time variation as the dipolarity of a dementia degree of the subject, wherein the statistic comprises a mean dipolarity indicating a mean value of a fixed number of peak values at a time when a plurality of dipolarities are obtain by sampling and a standard deviation indicating a fluctuation of the peak values, and whether the subject is normal or demented is estimated by a mutual relationship between the mean dipolarity and the standard deviation.

* * * * *

UNITED STATES PATENT AND TRADEMARK OFFICE
CERTIFICATE OF CORRECTION

PATENT NO.    : 6,741,888 B2
DATED         : May 25, 2004
INVENTOR(S)   : Toshimitsu Musha et al.

It is certified that error appears in the above-identified patent and that said Letters Patent is hereby corrected as shown below:

Column 10,
Line 13, please change "a in" to -- in a --.
Line 18, please change "statistical" to -- statistic --.

Column 12,
Line 17, please change "obtain" to -- obtained --.

Signed and Sealed this

Twenty-first Day of September, 2004

JON W. DUDAS
*Director of the United States Patent and Trademark Office*

UNITED STATES PATENT AND TRADEMARK OFFICE
CERTIFICATE OF CORRECTION

PATENT NO. : 6,741,888 B2
DATED : May 25, 2004
INVENTOR(S) : Toshimitsu Musha et al.

It is certified that error appears in the above-identified patent and that said Letters Patent is hereby corrected as shown below:

Column 10,
Line 57, after the first occurrence of "in", please insert -- a --.

Signed and Sealed this

Fifth Day of April, 2005

JON W. DUDAS
*Director of the United States Patent and Trademark Office*

UNITED STATES PATENT AND TRADEMARK OFFICE
CERTIFICATE OF CORRECTION

PATENT NO. : 6,741,888 B2
APPLICATION NO. : 09/993910
DATED : May 25, 2004
INVENTOR(S) : Toshimitsu Musha et al.

It is certified that error appears in the above-identified patent and that said Letters Patent is hereby corrected as shown below:

At column 10, line 56, after "impairment in " and before "brain", please insert --a--.
At column 10, line 57, after the first occurrence of "in", please insert --a--.

Signed and Sealed this

Twenty-ninth Day of August, 2006

JON W. DUDAS
*Director of the United States Patent and Trademark Office*